United States Patent [19]

Eaton

[11] 4,217,964
[45] Aug. 19, 1980

[54] FORWARD AND REVERSE ROTARY TOOL

[75] Inventor: Russell K. Eaton, Kalamazoo, Mich.

[73] Assignee: Stryker Corporation, Kalamazoo, Mich.

[21] Appl. No.: 525

[22] Filed: Jan. 2, 1979

[51] Int. Cl.² .......................... E21B 3/00; E21B 1/00
[52] U.S. Cl. ................................... 173/163; 192/21; 192/93 A; 192/95
[58] Field of Search ............... 173/163; 192/21, 93 A, 192/95

[56] References Cited

U.S. PATENT DOCUMENTS

| | | | |
|---|---|---|---|
| 2,435,536 | 2/1948 | Ferris | 192/21 X |
| 2,602,347 | 7/1952 | Miller | 192/21 |
| 3,539,044 | 11/1970 | Grimstad | 192/21 |
| 3,756,090 | 9/1973 | Meila et al. | 173/163 |
| 4,050,528 | 9/1977 | Foltz | 173/163 |
| 4,091,880 | 5/1978 | Troutner | 173/163 |
| 4,124,026 | 11/1978 | Berner et al. | 173/163 |
| 4,159,050 | 6/1979 | Hopkins et al. | 192/93 A |

Primary Examiner—Ronald Feldbaum
Attorney, Agent, or Firm—Blanchard, Flynn, Thiel, Boutell & Tanis

[57] ABSTRACT

Forward and reverse rotary tool, particularly for inserting and retracting a threaded element. The power-driven tool is designed primarily for surgical use and is capable of applying pressure against the free end of the threaded element during both the inserting and retracting operation, as into a bone. The shift from a driving mode to a retracting mode, or vice versa, is readily effected under conditions existing in an operating room. All movable and/or lubricated parts, other than the driven element, are housed to prevent leakage of lubricant. The tool comprises a unidirectionally driven pinion in constant engagement with a pair of counter-rotating clutch elements and means alternatively engageable with said clutch elements for rotative driving in one direction or the opposite direction.

9 Claims, 3 Drawing Figures

U.S. Patent     Aug. 19, 1980     4,217,964
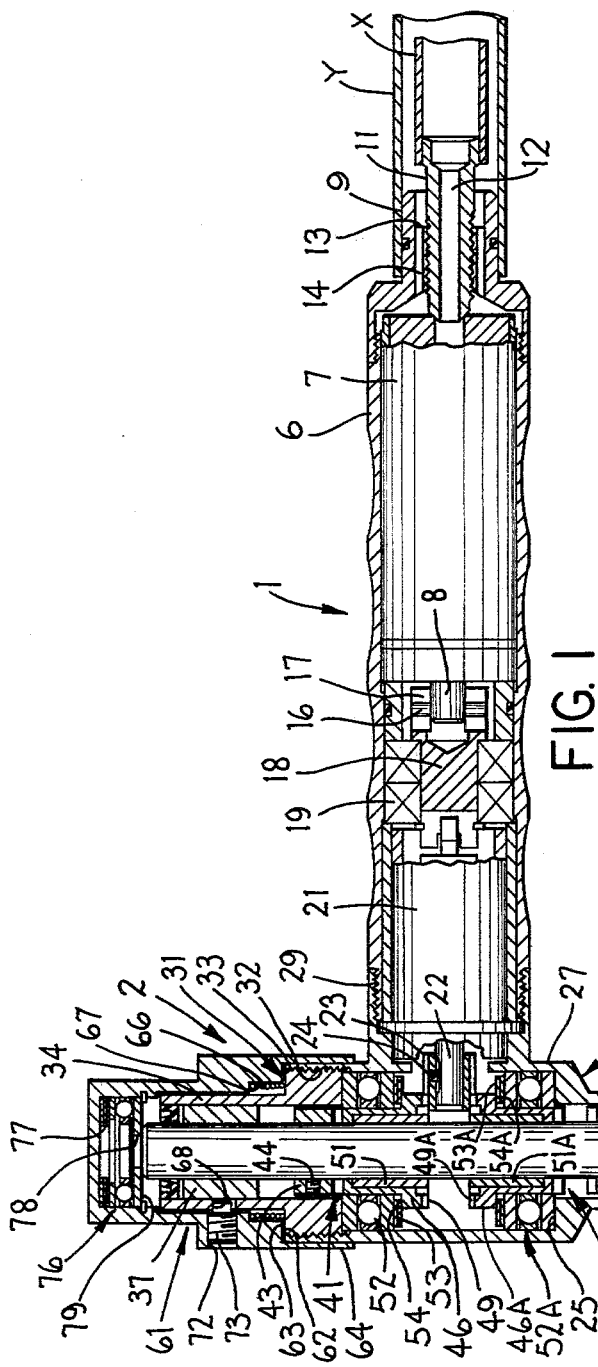
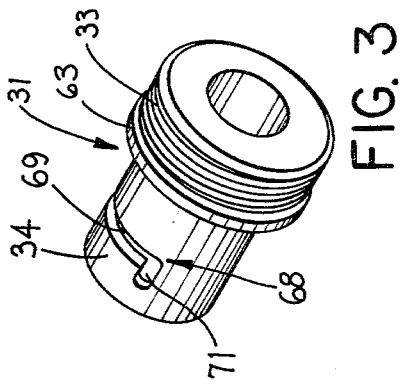
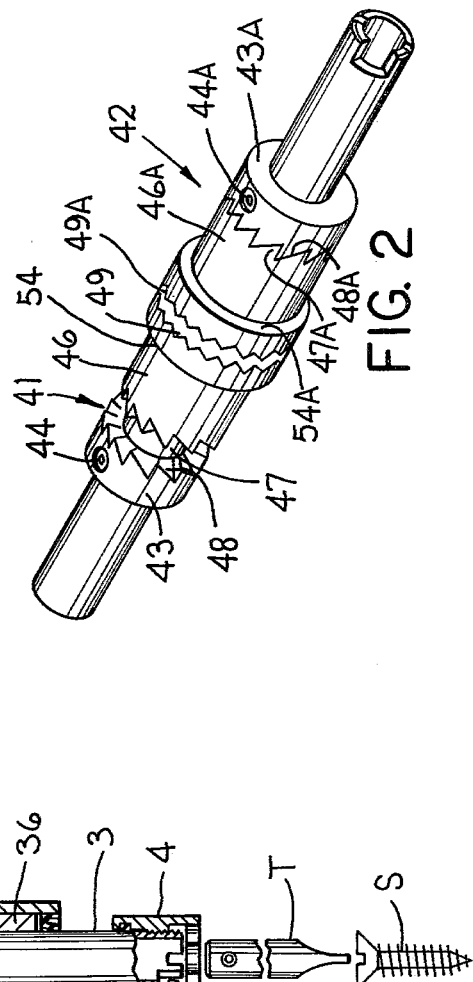

FORWARD AND REVERSE ROTARY TOOL

FIELD OF THE INVENTION

The invention relates to rotary tool driving means, particularly for surgical operation but not necessarily confined thereto, wherein rotatable tool engageable means may be driven under power in either direction of rotation and wherein the direction of such driving may be quickly and easily determined by manually operable means.

BACKGROUND OF THE INVENTION

The concept of mechanical means for driving rotative tools, such as drilling, tapping or screw driving means, is an old one and many, possibly thousands, of such means have been offered to the trade over a period of many years. These devices have been both hand and power driven and many of them have included both speed and directional control.

However, insofar as I am aware, the majority of these devices have been designed primarily for workshop or machine shop use and few, if any, of them are appropriate for surgical use. It is self-evident that mechanisms intended for surgical use must meet a wide variety of criteria that are not necessary for use in other environments and it is therefore equally self-evident that mechanisms devised for general use are not usually acceptable for surgical use. Among such criteria are driving by nonelectric means, providing a tool small enough to be light in weight, easy to handle and of minimum obstruction to the vision of the operator, full sealing against escape of lubricant and total enclosure of all working parts excepting only the tool engaging means and the direction selecting means.

Accordingly, the objects of the invention include:

1. To provide means for rotating a tool in either rotative direction in order to perform a drilling or tapping operation or to drive or remove screw means, for example.

2. To provide means, as aforesaid, wherein such rotative direction is maintained regardless of the direction of axial pressure upon the tool.

3. To provide means, as aforesaid, wherein the direction of rotation may be quickly and easily selected, capable of operation at a moment's notice by surgical personnel and further wherein such selection may be accomplished by the operator by feel rather than under the necessity of visual observation.

4. To provide a tool, as aforesaid, wherein the motor may be housed in the handle thereof whereby to minimize the diameter of the portion of the housing containing the driving mechanism, whereby to minimize the obstruction to vision presented over the operating area to the user of the tool.

5. To provide a rotary tool, as aforesaid, wherein all operating components are fully enclosed excepting only the part actually engaging the rotating tool and a manually operable part for selecting the direction of rotation of the tool.

6. To provide a device, as aforesaid, wherein all lubricated parts are effectively sealed against escape of lubricant.

Other objects and purposes of the invention will be apparent to persons acquainted with apparatus of this general type upon reading the following specification and inspection of the accompanying drawings.

BRIEF DESCRIPTION OF THE DRAWINGS

In the drawings:

FIG. 1 is a central section of a preferred device embodying the invention.

FIG. 2 is an oblique view of a detail of the clutch mechanism.

FIG. 3 is an oblique view of a detail of the direction selecting mechanism.

DETAILED DESCRIPTION

Turning now to the drawings and with principal reference, at least for the present, to FIG. 1, there is shown a device embodying the invention comprising broadly a handle section 1 and a gear and clutch section 2. Air motor means, hereinafter further identified, is contained within said handle section 1 and an output shaft 3 projects from the gear and clutch section 2 for driving by means of a conventional chuck 4 any desired threaded device or tool T.

Turning now to the apparatus in more detail, the handle section 1 comprises a casing 6 containing a conventional air motor 7 having an output shaft 8. The casing 6 carries at one end thereof, here the rightward end as appearing in FIG. 1, a pair of concentric hose fittings 9 and 11, the hose fitting 11 having a central opening 12 communicating from a supply hose X to the inlet of the motor 7 and the hose fitting 9 having a spider 13 for supporting the fitting 11. Said spider is provided with a plurality of openings of which one appears at 14 for connecting the outlet ports (not shown) of the motor 7 with the interior of the exhaust hose Y.

The output shaft 8 of the motor 7 is provided with a pin 16 radially therethrough which is received into a slot 17 of the coupling 18 whereby rotation of said shaft 8 will rotatively drive the coupling 18. The coupling 18 is rotatively supported in any suitable manner as by bearings 19 and is rotatively connected to any conventional speed reduction gearing 21. Said speed reduction gearing is provided with an output shaft 22 on which is mounted a drive pinion 23, said drive pinion being in this instance drivingly related to said shaft 22 by a set screw 24.

Turning now to the gear and clutch section 2, there is provided a lower housing 26 which is of a first diameter in a first portion 27 thereof and of a lesser diameter in a second portion 28 thereof. Said housing 26 is preferably, as here, fixed by threaded means 29 to the handle section 6. An upper housing portion 31 is threadedly related at 32 to the upper end of the housing 26 and also comprises portions of two diameters, namely a first diameter 33 which is here at least substantially equal to the diameter of the portion 27 of the lower housing 26 and a portion 34 of lesser diameter which is in this instance substantially equal to the diameter of the portion 28 of the housing 26.

Fixed within said portions 28 and 34, respectively, are a pair of sleeve bearings 36 and 37, said sleeve bearings being fixed within said housing portions in any convenient manner, as by press fitting. A shaft 3 is both rotatably and slidably received within and supported by said sleeve bearings in a manner and for purposes further developed hereinafter. One end (lower end as appearing in FIG. 1) of said shaft 3 carries the chuck 4 which chuck may as above indicated by fully conventional and adapted for receiving and firmly holding whatever kind of tool is desired to be driven by the device of the present invention. Such chucks being widely known and forming no part of the present invention, further detailing thereof is unnecessary and is hence omitted.

Concentric with said shaft 3 are two clutch units which for reference purposes herein may be identified as an upper clutch unit 41 and a lower clutch unit 42. Said upper clutch unit comprises a driven jaw clutch element 43 which is rigidly fixed as by a set screw 44 (FIG. 2) to the shaft 3 and a driving clutch element 46, said latter being provided with suitable tooth elements 47 (FIG. 2) for engaging the correspondingly toothed elements 48 of the driven clutch element 43. Said driving clutch element 46 is provided with axially directed teeth 49 which are in constant engagement with the teeth of pinion 23. Said driving clutch element 46 is here radially supported by a sleeve bearing 51 which is in turn supported on the shaft 3 and is axially fixed in position by a thrust bearing 52 located between the facing end of the upper housing portion 31 and a washer 53 which bears against a suitable shoulder 54 on the driving clutch element 46. Said thrust bearing 52 thus holds the teeth 49 of the driving clutch element 46 in driving engagement with the teeth of the pinion 23, whereby to effect constant rotation of said driving clutch element 46 regardless of the position of the shaft 3 with respect thereto.

The lower clutch element 42 is constructed and arranged similarly to the construction and arrangement of the upper clutch element 41. Specifically said lower clutch unit comprises a jaw clutch element 43A which is rigidly fixed as by a set screw 44A (FIG. 2) to the shaft 3 and a driving clutch element 46A, said latter being provided with suitable tooth elements 47A for engaging the correspondingly toothed elements 48A of the driven clutch element 43A. Said driving clutch element 46A is provided with axially directed teeth 49A which are in constant engagement with the teeth of pinion 23. Said driving clutch element 46A is here radially supported by a sleeve bearing 51A which is in turn supported on the shaft 3 and is axially fixed in position by a thrust bearing 52A located between the shoulder 25 of the lower housing 26 and a washer 53A which bears against a suitable shoulder 54A on the driving clutch element 46A. Said thrust bearing 52A thus holds the teeth 49A of the driving clutch element 46A in driving engagement with the teeth of the pinion 23 whereby to effect constant rotation of said driving clutch element 46A regardless of the position of the shaft 3 with respect thereto.

Turning now to the means for selecting the rotative direction, there is provided a cap 61 telescopically received over the upper housing 31 and axially slidably related thereto. Said cap has an internal shoulder 62 facing and positioned close to an axially facing shoulder 63 of the upper housing meber 31 and said cap further has an elongated skirt 64 telescopically arranged around the upper end of the lower housing 26. A spring 66 is captured between said face 63 and a downwardly facing shoulder 67 of said cap.

An L-shaped slot 68 (FIG. 3) is provided in said upper housing section 31, said slot having a circumferential portion 69 which is arranged circumferentially of said casing section in a plane perpendicular to the axis thereof. Said slot also has an axial section 71 which is arranged in a plane through the axis of said housing 31. The cap 61 is provided with a threaded opening 72 which contains a pin 73 threaded thereinto whose pilot tip is received within said slot 68 for purposes appearing further hereinafter.

The upper end of said cap 61 contains a thrust bearing 76 which is held on one side by spacers 77 and on the other side by a washer 78. Said washer is positioned for contact by the upper end of the shaft 3 but axial movement thereof in the direction of said shaft is limited by a snap ring 79. Thus, axial movement of said shaft 3 upwardly is limited by the washer 78 acting against the thrust bearing 76 while rotation of said shaft is still permitted by said last-named bearing.

In considering now the operation of the apparatus, let us for the sake of illustration assume that same is to be used to insert a screw temporarily into a bone for holding same in a predetermined position while other work is being performed thereon and that said screw is later, either in the same operation or in a subsequent one, to be removed under conditions which will require the application of power thereto.

With the screw, partially and schematically indicated at S, and a screw driving tool T fixed to the chuck 4, the cap 61 is rotated appropriately to permit the pilot screw 73 to enter the axial portion 71 of the slot 68. This permits said cap to respond to the spring 66 and move axially upwardly. Thus, when the screw S is placed against the bone into which it is to be inserted and even a relatively light pressure exerted thereon, it will cause the shaft 3 to move upwardly until the upwardly facing jaw clutch elements of the driven clutch member 43A engage said downwardly facing jaw clutch elements of the driving clutch member 46A. Since the teeth 49A of the latter-named driving member are constantly engaged with the teeth of the pinion 23, this will, as soon as the motor 7 is caused to rotate, effect rotation of the shaft 3 and consequently appropriate rotation of the screw S.

When it is desired to retract said screw, the cap 61 will be moved downwardly against the spring 66 and rotated to move the pilot 73 into the circumferential portion 69 of the slot 68. This causes the washer 78 to contact the upper end of the shaft 3 and drive it downwardly, thus both engaging the respective jaw clutch teeth of the driven clutch element 43 and the driving clutch element 46 and disconnecting the jaw clutch teeth of the lower driven element 43A and lower driving element 46A. Now, rotation of the motor 7 will effect rotation of the shaft 3 in the opposite direction and will do so regardless of the direction of axial thrust between the shaft 3 and the screw S. Thus, regardless of whether said shaft and the chuck carried thereby is pressed against said screw or tends to be drawn away therefrom, rotation in a reverse direction will take place. The screw is thus retracted.

The operation of the tool for other purposes, such as drilling and/or tapping or driving a Steinman pin, will be obvious from the foregoing.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a rotary tool driving device having a handle, a clutch and gear housing fixed to said handle and a power output shaft axially within and projecting from said clutch and gear housing, the combination comprising:

a pinion rotatably supported adjacent said shaft and positioned with its axis at least substantially perpendicular to the axis of said shaft and means including prime mover means within said handle for driving said pinion;

a pair of clutch means each having driving and driven elements thereof and including connecting means drivingly connecting said elements of each of said pair of clutch means, the driving element of each of said pair of clutch means being in permanent mesh with said pinion and supported on, and for rotation with respect to, said shaft and means restraining each of said driving elements from axial movement with respect to said housing, and each of said driven elements being fixed to said shaft and spaced thereon a distance greater than the spacing of the respectively adjacent connecting means on said driving elements;

said shaft being axially slidable in said housing and with respect to said driving elements whereby in one axial position thereof one of said driven elements will drivingly engage its corresponding driving element for effecting rotation of said shaft in one direction and in another axial position of said shaft the other driven element will engage in driving relationship its corresponding driving element for effecting rotation of said shaft in the opposite direction; and manually operable means for holding said shaft in a selected one of said axial positions.

2. The device of claim 1 wherein said manually operable means comprises a cap supported on, and axially movable with respect to, said housing and abutment means associated with said cap for bearing against a portion of said shaft for holding said shaft in one selected position.

3. The device of claim 2 wherein said manually operable means comprises a pin and slot arrangement which in one rotative position of said cap will permit axial movement thereof with respect to said housing and in a different rotative position of said cap will hold said cap against such axial movement and in position for holding said shaft in said selected position.

4. The device of claim 3 wherein said pin and slot means comprises an L-shaped slot within said housing wherein one leg thereof is parallel to the axis of said housing and the other leg is in a plane perpendicular thereto and wherein said pin is fixed within said cap and includes a pilot element extending into said slot.

5. The device of claim 2 wherein said abutment means comprises a thrust bearing within said cap and means positioned operatively between said thrust bearing and said shaft for engaging said shaft and holding same in said one selected position.

6. The device of claim 2 including also resilient means acting between said housing and said cap for normally urging said cap axially thereof from the position wherein it holds said shaft in one selected position.

7. The device of claim 4, including also resilient means acting between said housing and said cap, same being positioned normally to urge said cap in a direction parallel to the axis of said housing and away from that positon in which said pin may enter into said other leg.

8. The device of claim 1 wherein said prime mover means consists of an air-driven motor and speed reducing means both mounted within said handle, the output of said speed reducing means being drivingly connected to said pinion.

9. The device defined in claim 2 wherein said cap includes also a skirt projecting therefrom and telescoping with said housing for overlapping same in all positions of said cap with respect to said housing whereby to inhibit the entry of dirt into the interior of said cap.

* * * * *